US009758101B2

(12) United States Patent
Clair-Chalupka (10) Patent No.: US 9,758,101 B2
(45) Date of Patent: Sep. 12, 2017

(54) HAND SANITIZER FOR VEHICLES (71) Applicant: Dimitri Clair-Chalupka, Santa Barbara, CA (US)

(72) Inventor: Dimitri Clair-Chalupka, Santa Barbara, CA (US)

( * ) Notice: Subject to any disclaimer, the term of this patent is extended or adjusted under 35 U.S.C. 154(b) by 0 days.

(21) Appl. No.: 15/154,918

(22) Filed: May 13, 2016

(65) Prior Publication Data
US 2016/0362051 A1  Dec. 15, 2016

Related U.S. Application Data (60) Provisional application No. 62/160,907, filed on May 13, 2015.

(51) Int. Cl.
| | | |
|---|---|---|
| *B60R 1/12* | (2006.01) | |
| *B60R 1/04* | (2006.01) | |
| *A61L 2/16* | (2006.01) | |
| *A47K 5/00* | (2006.01) | |
| *B60R 15/02* | (2006.01) | |
| *A47K 5/12* | (2006.01) | |

(52) U.S. Cl.
CPC  *B60R 1/12* (2013.01); *A61L 2/16* (2013.01); *B60R 1/04* (2013.01); *B60R 15/02* (2013.01); *A47K 5/1211* (2013.01); *A47K 5/1217* (2013.01); *A61L 2202/15* (2013.01); *A61L 2202/16* (2013.01)

(58) Field of Classification Search
CPC ......... B60R 1/12; B60R 1/02; A61L 2202/16; A47K 3/281
USPC .......................................... 359/844; 222/192
See application file for complete search history.

(56) References Cited

U.S. PATENT DOCUMENTS

| | | | |
|---|---|---|---|
| 6,428,172 B1 | 8/2002 | Hutzel | |
| 6,902,284 B2 | 6/2005 | Hutzel | |
| 7,178,693 B1 * | 2/2007 | Cutrone | A47K 5/1202 222/135 |
| 2003/0117728 A1 * | 6/2003 | Hutzel | B60Q 3/023 359/838 |
| 2006/0119235 A1 * | 6/2006 | Aisley | A47B 47/00 312/242 |
| 2012/0112914 A1 * | 5/2012 | Wegelin | A47K 5/1217 340/573.1 |
| 2012/0120239 A1 | 5/2012 | Hutzel | |
| 2013/0262345 A1 * | 10/2013 | Ciavarella | A61L 2/0088 705/500 |
| 2015/0157176 A1 * | 6/2015 | Muderlak | A47K 5/1217 222/333 |

FOREIGN PATENT DOCUMENTS

| | | | | |
|---|---|---|---|---|
| GB | 2417422 A | * | 3/2006 | ............ A61L 9/048 |
| KR | 2002063065 A | * | 8/2002 | |
| KR | 2002066142 A | * | 8/2002 | |
| WO | WO 02/26066 A1 | * | 4/2002 | |

\* cited by examiner

*Primary Examiner* — Daniel J Colilla
(74) *Attorney, Agent, or Firm* — Guy Cumberbatch (57) ABSTRACT

A dispenser for, e.g., hand sanitizer or perfume mounted within a rear view mirror of a vehicle. The dispenser has a manual or automated mechanism that expels a small amount of hand sanitizer at a time, preferably when a person places his or her hand under the mirror. The dispenser includes a replaceable reservoir, dispensing mechanism, power source and control circuitry within a cavity in the mirror. A front mirror panel may be hinged to enable access to the operational components.

20 Claims, 7 Drawing Sheets

HAND SANITIZER FOR VEHICLES

RELATED APPLICATIONS

The present claims priority under 35 U.S.C. §119 to U.S. Provisional Application Ser. No. 62/160,907, filed May 13, 2015.

FIELD OF THE INVENTION

The present invention relates generally to a hand sanitizer dispenser for a vehicle and, more particularly, a dispenser mounted within a rear view mirror.

BACKGROUND OF THE INVENTION

Recently, electronic, electric and various additional functional features have been added to the rearview mirror assembly, for example map reading lights, reflective elements with displays, controls for actuating garage doors, or the like, which have consumed much of the available space in the interior rearview mirror assembly. However, with the advent of electro-optic mirrors, such as electrochromic mirrors, a new generation of rearview mirrors has afforded the possibility of a slim reflector package. Since a day/night actuator mechanism is no longer needed in such mirrors, the size of the reflective element assembly is defined by the thickness of the electrochromic mirror element and by its associated electronics, thereby decreasing the profile of the mirror assembly or, conversely, affording room within the assembly for additional functions. U.S. Pat. No. 7,293,888 discloses various accessories for rear views mirrors such as the provision of storage space for a pair of eyeglasses, a writing pad, a cell phone, a courtesy light, or a video screen that can be pulled out to depend below the mirror.

Despite some advances in this area, there is a need for added functionality of the standard dashboard, and in particular the rear view mirror, that is within easy reach of the driver.

BRIEF DESCRIPTION OF THE DRAWINGS

Features and advantages of the present invention will become appreciated as the same become better understood with reference to the specification, claims, and appended drawings wherein:

DETAILED DESCRIPTION OF THE PREFERRED EMBODIMENTS

The present invention provides a dispenser for, e.g., hand sanitizer or perfume mounted within a rear view mirror of a vehicle. The exemplary dispenser includes an automated mechanism that expels a small amount of hand sanitizer at a time, preferably when a person places his or her hand under the mirror.

Figure 1:
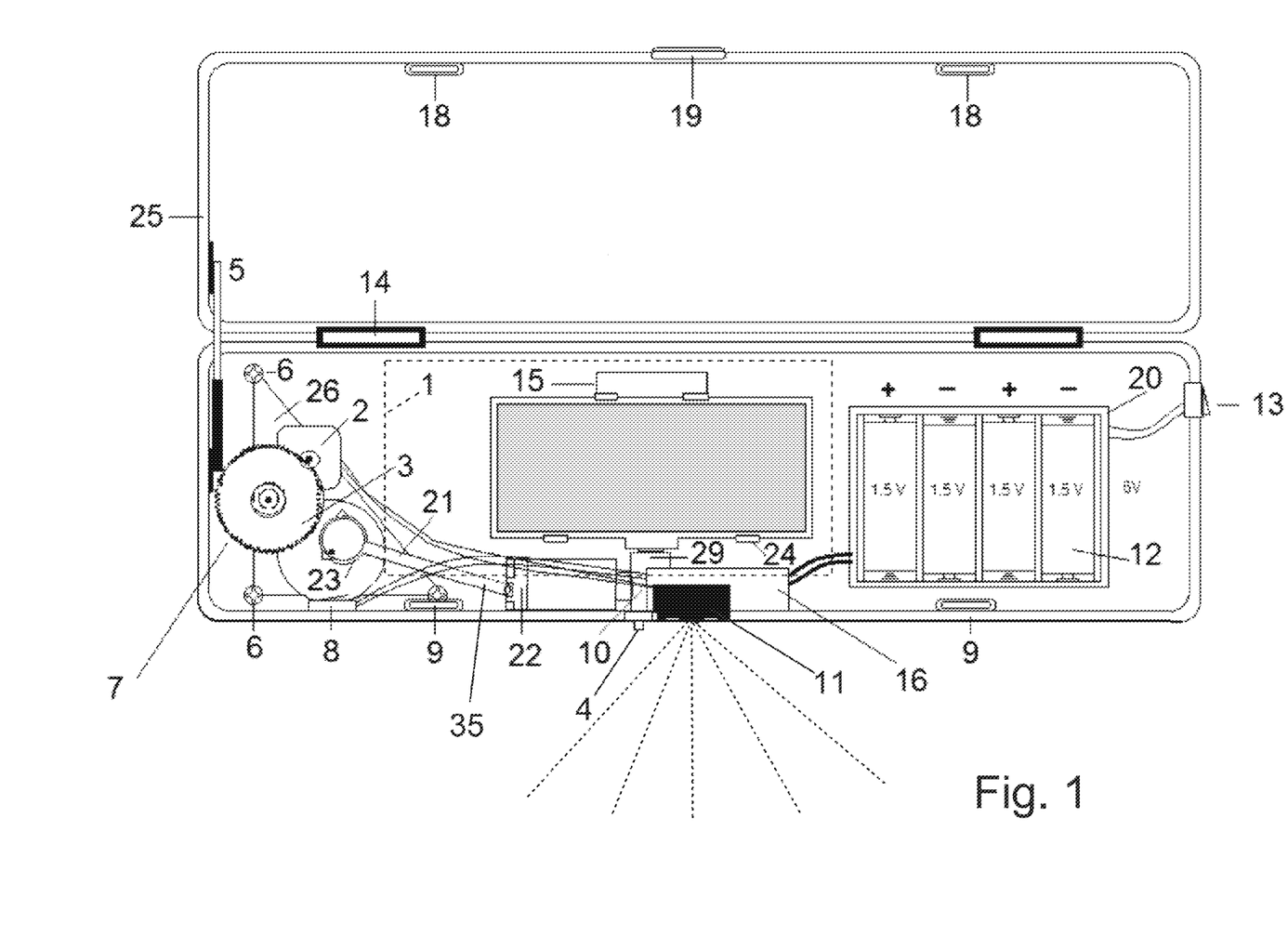
FIG. 1 is a front view of a hand sanitizer dispenser mounted in a rear view mirror with a front mirror panel lifted open to show an operating mechanism therein.
Figure 2A:
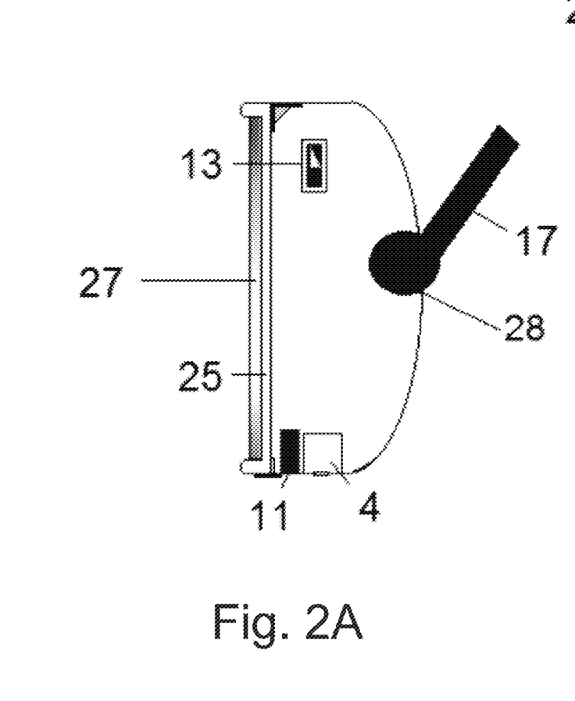
FIG. 2A is a right side view of the hand sanitizer dispenser with a front mirror panel of the rear view mirror in a closed position.
Figure 2B:
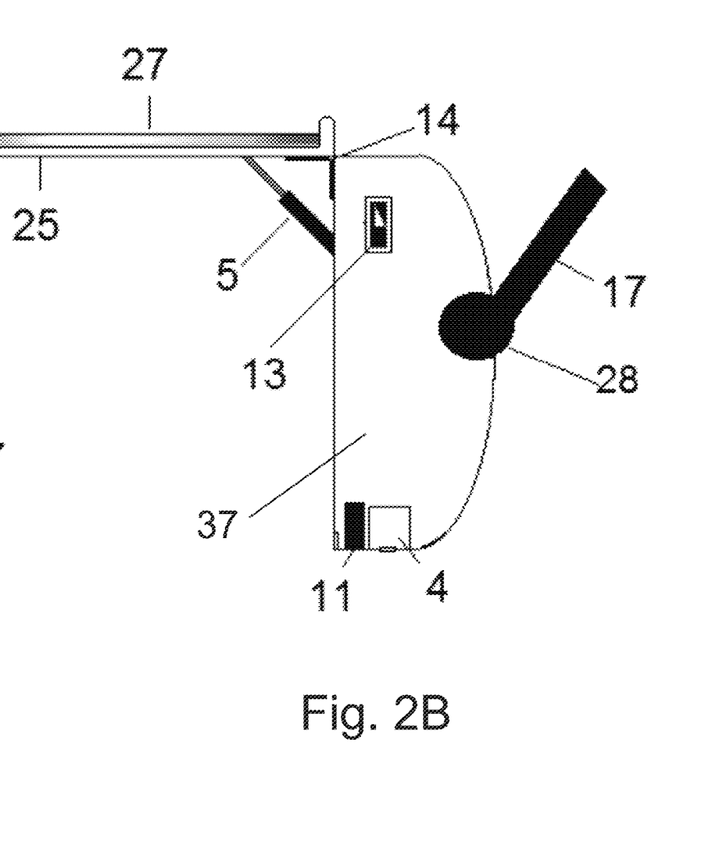
FIG. 2B is a right side view of the hand sanitizer dispenser with the front mirror panel in an open position.
Figure 3:
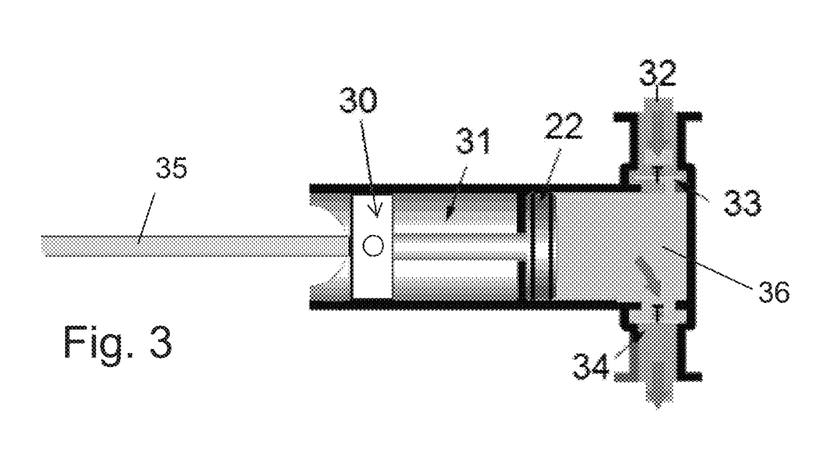
FIG. 3 is a close-up view of an automated piston mounted in the rear view mirror used to propel hand sanitizer from an outlet port.

Various components of the mirror and dispenser that are shown in FIGS. 1-3 are numbered below:
1. Tank antibacterial gel form of replaceable cartridge (in phantom)
2. Electric motor 6v
3. Gear system composed of three toothed wheels and a connecting rod
4. Gel dispensing nozzle
5. Piston/cylinder for opening the door
6. Maintaining holder screw gear device
7. Toothed wheel of the gear arrangement
8. Limit Switch
9. Magnetic lock of the (fixed part)
10. Gel spillway tube
11. Presence detector
12. Rechargeable 1.5 volt LR03 battery quantity: 4
13. Start switch on/off type: on/off
14. Hinge, piano-type
15. Mobile device charging gel blocking (with push lever return spring)
16. Electronic Map
17. Mirror arm support
18. Magnetic closure (moving part)
19. The door lock device
20. Batteries Housing Support
21. Arm piston lever action
22. Piston head
23. Toothed wheel of the gear arrangement
24. Cartridge-holder locking device (Fixed)
25. Door mirror support panel
26. Support plate (embase), for gear device
27. Reflecting mirror
28. Mirror position adjustment ball
29. Drilling device for the lid of the antibacterial gel recharge
30. Flex coupling
31. Piston shaft (Crosshead)
32. Suction
33. Suction valve
34. Discharge valve
35. Crankshaft
36. Mirror body With reference to FIGS. 1-3, a replaceable tank 1 of hand sanitizer liquid such as an alcohol-based liquid or gel (e.g., isopropyl alcohol (isopropanol), ethanol, n-propanol, or povidone-iodine) fits within a cavity inside the rear view mirror body 37. The tank 1 is shown in phantom so as not to block the view of other functional components. To insert, remove and replace the tank, the mirror 27 is supported by a support panel 25 mounted via horizontal piano-type hinges 14 at a top edge of the body 37. The panel 25 and mirror 27 swing outward to access the inner cavity, and are preferably supported open in the position of FIG. 3 by one or more piston/cylinder combinations 5. The panel 25 may be held in the closed position of FIG. 2 by magnetic closures 9.

Figure 4:
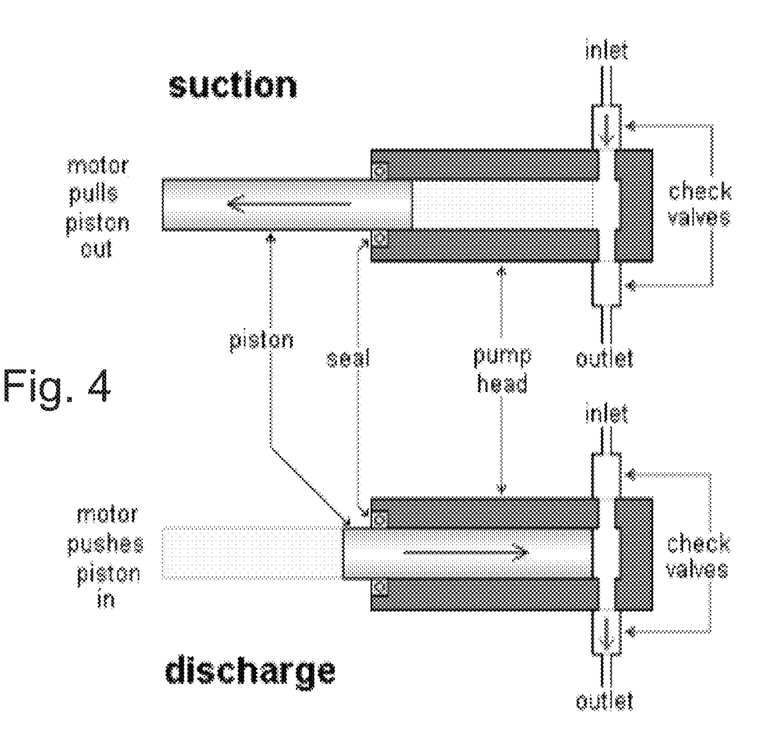
FIG. 4 schematically shows the functioning of the automated piston to discharge hand sanitizer from an outlet port.
Figure 5A:
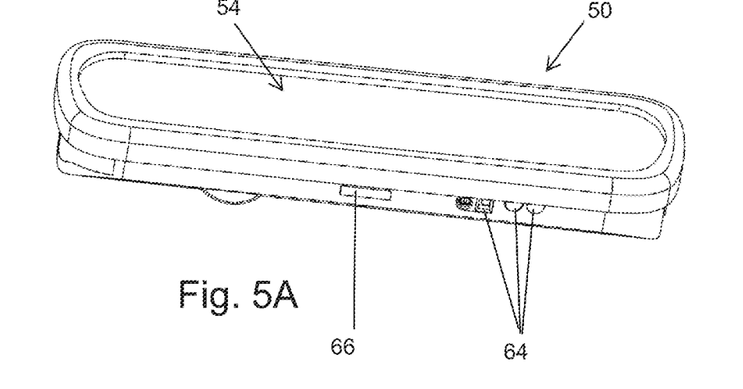
FIGS. 5A-5D are perspective views of an exemplary outer shape of the rear view mirror of the present application.
Figure 5B:
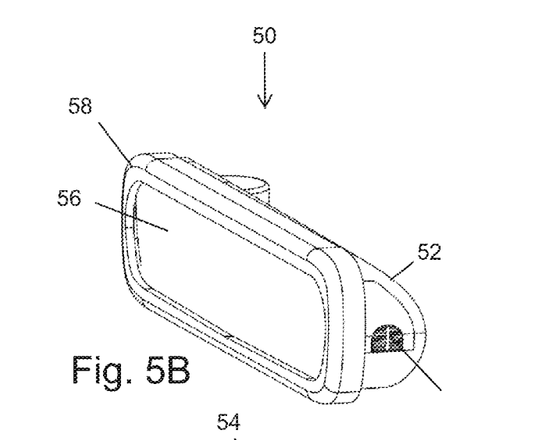
Figure 5C:
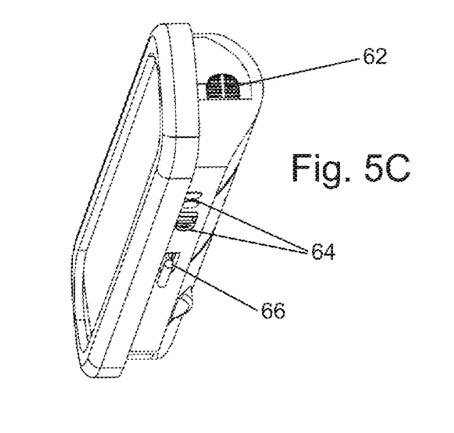
Figure 5D:
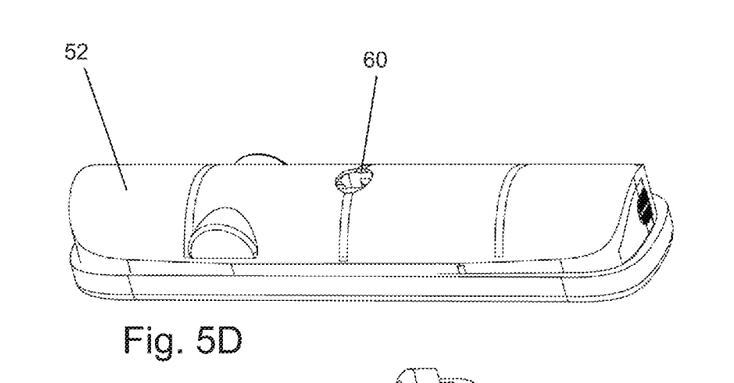

A proximity detector 11 detects the user's hand and sends a signal to the motor 2. The motor 2 in turn rotates 180°, which pulls the piston 22 out of a transfer chamber 36, as seen in FIGS. 3 and 4, pulling gel from the tank 1 through a suction valve 33 into the chamber. The motor 2 then continues another 180° and pushes the piston 22 in, which urges the gel from the chamber 36 through a discharge valve 35, and through a spillway tube 10 and dispensing nozzle 4 (see FIG. 1) so as to discharge the hand sanitizer on the user's hand. Circuitry for the motor 2 limits its rotation to 360° in any one dispensing cycle, and to help avoid mess, the circuitry immediately stops the motor 2 when the user's hand is removed from under the mirror, even mid-stroke. Of course, a manual override such as a switch of sorts may be included so that hand sanitizer is not inadvertently dispensed.

Although a proximity detector 11 coupled to an automatic dispenser mechanism is preferred, a manual dispenser may also be used. In such case, actuation of a lever or button on the lower edge of the mirror desirably causes a small quantity of hand sanitizer to discharge on the user's hand. Of course, this simplifies the mechanism so that electronics and pumps are not needed.

FIG. 3 shows a typical automated piston type of dispensing mechanism used to propel hand sanitizer from an outlet port that may be mounted in the rear view mirror cavity. A crankshaft 35 that may be driven by a reciprocating wheel (not shown) on its left end displaces a piston shaft 31 through a flex coupling 30. A piston head 22 moves within a sealed end of a cylinder and creates positive and negative pressures therein to cooperate with a suction valve 33 and a discharge valve 34. The basic principles are illustrated in FIG. 4. Alternatively, a peristaltic pump which forces fluid through flexible tubing using a rotating wheel may be used. Either of these systems, or others, may be termed "powered pumps" or "powered mechanisms" in that they are actuated by a motor or other such powered device.

FIGS. 5A-5D are perspective views of an exemplary outer shape of a rear view mirror 50 of the present application. The mirror 50 includes a mirror body 52 defining a cavity (not shown) therein. A front mirror panel 54 comprises a mirror 56 surrounded by a rounded rectangular bezel 58. As described above, the front mirror panel 54 is desirably hinged to allow it to swing open and access the inner contents of the cavity, such as for refilling a hand sanitizer reservoir.

In a preferred embodiment, the mirror body 52 has a convex rear side in which is formed a mounting hole 60 that receives a mounting stalk (not shown). A small vent 62 on one end wall of the mirror body 52 may be provided. Control buttons 64 and a hand sanitizer dispenser nozzle 66 are arranged along a lower edge.

Figure 6:
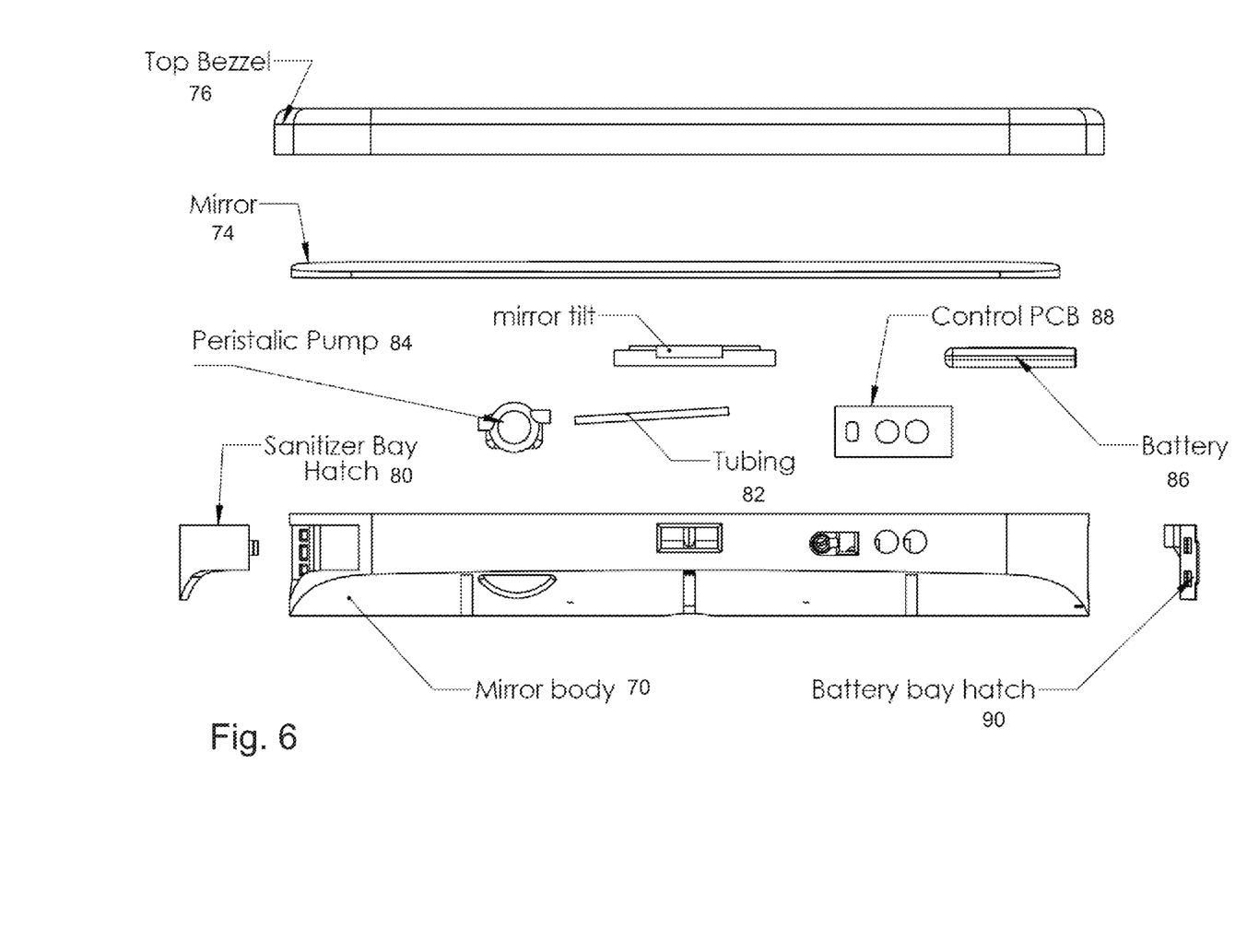
FIG. 6 is an exploded view of an exemplary rear view mirror showing several internal operational components.

FIG. 6 is an exploded view of another exemplary rear view mirror showing several internal operational components. As before, a mirror body 72 defines a cavity (not numbered) in which the operational components are mounted. The cavity is covered by a front mirror panel comprising a mirror 74 and a surrounding bezel 76. In this embodiment, a hand sanitizer dispenser is provided on one lateral and of the mirror body. In particular, a sanitizer bay hatch 80 covers an opening in which a dispenser reservoir (not shown) connects to a length of tubing 82 which passes through a peristaltic pump 84. The peristaltic pump 84 has a small motor that is energized by a battery 86 and controlled through a circuit board 88. On the opposite end of the mirror body 72 from the sanitizer bay hatch 80, a removable battery bay hatch 90 is provided for replacement of the battery 86. In this embodiment, a hand sanitizer dispensing nozzle (not shown) may be provided anywhere along the lower edge of the mirror body 72.

Figure 7:
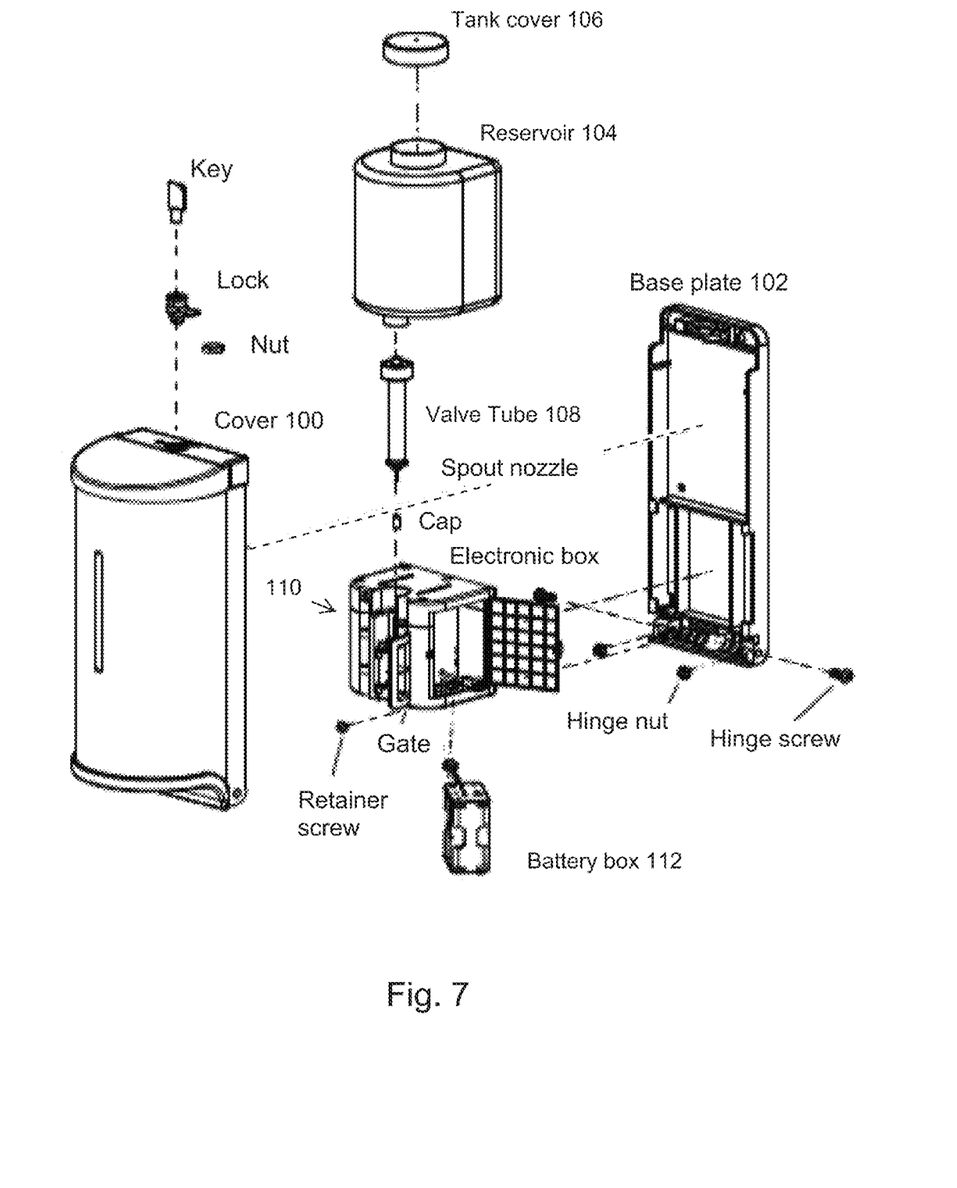
FIG. 7 is an exploded view of one version of a hand sanitizer dispenser mechanism.

FIG. 7 is an exploded view of one version of a hand sanitizer dispenser mechanism that may be utilized within the rear view mirrors described herein. The mechanism includes an outer cover 100 that defines a cavity (not shown) therein covered by a base plate 102. A hand sanitizer reservoir 104 having a cover 106 connects to a short section of tubing 108 that passes through a peristaltic pump 110. Although not shown, the pump 110 includes electronics powered by a battery 112 that squeeze the tubing 108 to dispense hand sanitizer through a nozzle at the lower end. Although a refillable reservoir 104 is shown, cartridges or other such replaceable reservoirs may be utilized.

Figure 8:
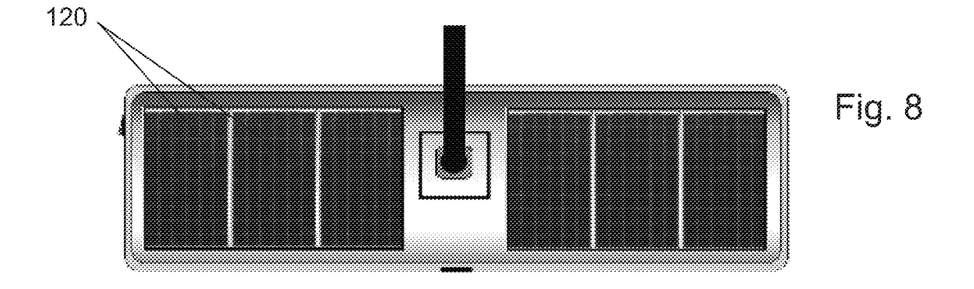
FIG. 8 is a rear view of a mirror of the present application showing solar panels thereon.

FIG. 8 is a rear view of a mirror of the present application showing solar photovoltaic panels 120 thereon. The panels 120 are on a rear side of the mirror so that they face the windshield and are exposed to maximum sunlight. The panels 120 may be used to power the hand sanitizer dispensing mechanism directly, or to charge an internal battery.

It should also be understood that other fluids than hand sanitizer could be dispensed by the mechanism disclosed herein. For instance, cologne, glass cleaner, or some other fluid may be used that preferably requires just a small amount and will not create too much mess if inadvertently dispensed into the car.

Figures 9A, 9B, 9C:
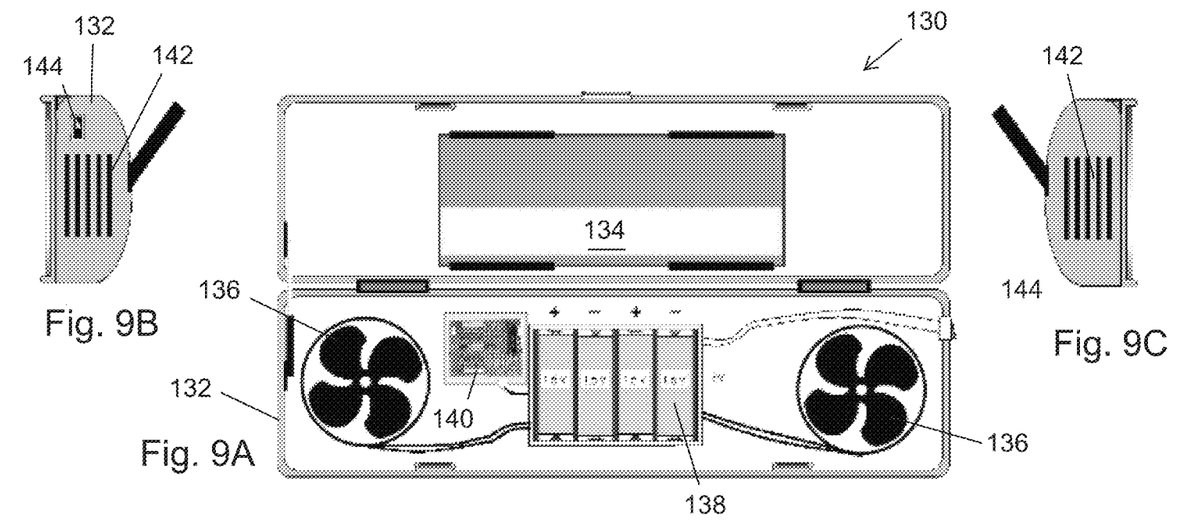
FIGS. 9A-9C are several views of an alternative rear view mirror of the present application having a perfume dispenser therein.

For instance, FIGS. 9A-9C show several views of an alternative rear view mirror 130 of the present application having a perfume dispenser therein. As before, a mirror body 132 defines a cavity in which is provided a perfume reservoir 134 and a pair of small fans 136. The fans 136 are driven by motors (not shown) which are powered by batteries 138 and controlled by a circuit board 140. Vents 142 in both ends of the mirror body 132 permit release of the perfume when a switch 144 is activated to turn on the fans 136. The switch 144 also may activate a pump or other such dispensing mechanism to release a small quantity of the perfume in the reservoir 134. The perfume dispenser may be provided in place of or in addition to the hand sanitizer dispenser.

In the preferred embodiment, as illustrated, the rear view mirror is mounted to the front windshield or vehicle ceiling just above the front windshield and is the primary rear view mirror. However, other mirrors within vehicles may be modified to include the hand sanitizer dispenser described herein. In one embodiment, one or both of the side view mirrors outside of the passenger compartment include the hand sanitizer dispenser of the present application. Providing the dispenser on the outside of the vehicle in this manner avoids any possible drips dirtying the interior. In the side-view mirror embodiment, the panel that opens to refill the hand sanitizer may be provided with a lock or other security barrier to prevent unauthorized access. It should therefore be noted that the term "rear view mirror" refers to not only the primary centrally located mirror on the dashboard, but any mirror used in vehicles for rear view visibility.

It should also be understood that the hand sanitizer dispenser described herein can also be incorporated into other vehicular objects, such as in the overhead visors or under the glove compartment.

The rear view mirror dispensers disclosed herein may be provided with new vehicles, or may be after-market devices that can replace an existing mirror. The variety of vehicles that can accommodate the rear view mirror dispensers is essentially unlimited, though the devices are particularly useful in high use vehicles such as taxis or buses.

While the invention has been described in its preferred embodiments, it is to be understood that the words that have been used are words of description and not of limitation. Therefore, changes may be made within the appended claims without departing from the true scope of the invention.

What is claimed is:

1. A rear view mirror for a vehicle having a hand sanitizer dispenser, comprising:
    a rear view mirror body having a front mirror panel thereon, wherein the mirror body is connected to a mirror arm support configured for mounting to the windshield or vehicle ceiling above the windshield and the mirror is the primary rear view mirror for the vehicle;
    a cavity defined within the mirror body, wherein the front mirror panel is connected to the mirror body to be lifted and enable access to the cavity;
    a fluid dispenser mounted within the cavity containing hand sanitizer, the fluid dispenser including a removable or refillable reservoir containing hand sanitizer;
    a lower outlet from the fluid dispenser open to an underside of the mirror body; and
    a powered pump mechanism mounted within the cavity for expelling the hand sanitizer from the fluid dispenser through the lower outlet.

2. The rear view mirror of claim 1, further including one or more solar photovoltaic panels on a rear face of the mirror that supply electricity for the powered pump mechanism.

3. The rear view mirror of claim 1, wherein the mechanism for expelling the hand sanitizer includes a manual actuator.

4. The rear view mirror of claim 1, wherein the front mirror panel is hinged to the mirror body.

5. The rear view mirror of claim 4, further including magnetic latches for holding the front mirror panel closed against the mirror body.

6. The rear view mirror of claim 1, further including a proximity detector on a lower edge of the mirror body adjacent the lower outlet adapted to detect a user's hand and send a signal to dispense hand sanitizer through the lower outlet.

7. The rear view mirror of claim 6, further including circuitry that immediately stops dispensing of hand sanitizer when the user's hand is removed from under the mirror.

8. The rear view mirror of claim 1, wherein the powered pump mechanism includes a peristaltic pump with a rotating wheel which forces hand sanitizer through flexible tubing in fluid communication with the reservoir of hand sanitizer.

9. The rear view mirror of claim 1, wherein the powered pump mechanism includes a piston-cylinder arrangement in fluid communication with the reservoir of hand sanitizer, and a motor that drives the piston.

10. A rear view mirror for a vehicle having a hand sanitizer dispenser, comprising:
    a rear view mirror body having a cavity defined therewithin and a front mirror panel thereon, the front mirror panel being hinged to enable it to be pivoted away from the mirror body to enable access to the cavity, wherein the mirror body is connected to a mirror arm support configured for mounting to the windshield or vehicle ceiling above the windshield and the mirror is the primary rear view mirror for the vehicle;
    a hand sanitizer dispenser mounted within the cavity containing hand sanitizer;
    a battery and circuitry mounted within the cavity; and
    a powered mechanism including a powered pump mounted within the cavity and connected to the battery and circuitry for expelling the hand sanitizer from the hand sanitizer dispenser.

11. The rear view mirror of claim 10, further including magnetic latches for holding the front mirror panel closed against the mirror body.

12. The rear view mirror of claim 10, further including a proximity detector on a lower edge of the mirror body adapted to detect a user's hand and send a signal to dispense the hand sanitizer.

13. The rear view mirror of claim 12, wherein the mechanism for expelling the hand sanitizer includes a lower discharge outlet on the lower edge of the mirror body adjacent the lower discharge outlet through which the hand sanitizer is dispensed.

14. The rear view mirror of claim 13, further including circuitry that immediately stops dispensing of hand sanitizer when the user's hand is removed from under the mirror.

15. The rear view mirror of claim 10, further including one or more solar photovoltaic panels on a rear face of the mirror that supply electricity for the powered mechanism.

16. The rear view mirror of claim 10, wherein the powered pump includes a peristaltic pump with a rotating wheel which forces hand sanitizer through flexible tubing in fluid communication with a tank of hand sanitizer.

17. The rear view mirror of claim 10, wherein the powered pump includes a piston-cylinder arrangement in fluid communication with a tank of hand sanitizer, and a motor that drives the piston.

18. The rear view mirror of claim 17, wherein the circuitry limits rotation of the motor so as to avoid inadvertently dispensing hand sanitizer.

19. The rear view mirror of claim 17, wherein the tank of hand sanitizer is replaceable when the front mirror panel is pivoted away from the mirror body to enable access to the cavity.

20. A rear view mirror for a vehicle having a fluid dispenser, comprising:
    a rear view mirror body having a cavity defined therewithin and a front mirror panel thereon, the front mirror panel being hinged to enable it to be pivoted away from the mirror body to enable access to the cavity;
    a fluid dispenser mounted within the cavity containing fluid;
    a battery and circuitry mounted within the cavity; and
    a powered mechanism mounted within the cavity and connected to the battery and circuitry for expelling the fluid from the fluid dispenser, wherein the fluid is perfume and the powered mechanism is at least one fan within the cavity and further including vents in the mirror body for dispersing the perfume.

* * * * *